US012384921B2

(12) United States Patent
Schierlmann et al.

(10) Patent No.: US 12,384,921 B2
(45) Date of Patent: Aug. 12, 2025

(54) AIR PURIFYING COATING SYSTEM AND METHOD FOR MAKING SAME

(71) Applicant: BONA AB, Malmö (SE)

(72) Inventors: John F Schierlmann, Waxhaw, NC (US); Pietrina Peshel, Indian Trail, NC (US); Erica Lawson, Murfreesboro, TN (US); John Carey Banks, Monroe, NC (US)

(73) Assignee: BONA AB, Malmo (SE)

( * ) Notice: Subject to any disclaimer, the term of this patent is extended or adjusted under 35 U.S.C. 154(b) by 207 days.

(21) Appl. No.: 17/928,547

(22) PCT Filed: Jun. 3, 2021

(86) PCT No.: PCT/US2021/035718
§ 371 (c)(1),
(2) Date: Nov. 29, 2022

(87) PCT Pub. No.: WO2021/247875
PCT Pub. Date: Dec. 9, 2021

(65) Prior Publication Data
US 2023/0212406 A1    Jul. 6, 2023

Related U.S. Application Data

(60) Provisional application No. 63/034,143, filed on Jun. 3, 2020.

(51) Int. Cl.
| | | |
|---|---|---|
| *C11D 1/72* | (2006.01) | |
| *B01D 53/72* | (2006.01) | |
| *B01D 53/77* | (2006.01) | |
| *C09D 5/00* | (2006.01) | |
| *C09D 5/14* | (2006.01) | |
| *C09D 7/61* | (2018.01) | |
| *C11D 3/37* | (2006.01) | |
| *C11D 3/48* | (2006.01) | |

(52) U.S. Cl.
CPC ............... *C09D 5/00* (2013.01); *B01D 53/72* (2013.01); *B01D 53/77* (2013.01); *B01D 2251/602* (2013.01); *B01D 2255/20707* (2013.01); *B01D 2255/20792* (2013.01); *B01D 2257/708* (2013.01); *B01D 2258/06* (2013.01); *B01D 2259/4508* (2013.01); *B01D 2259/802* (2013.01)

(58) Field of Classification Search
CPC ........... C11D 1/72; C11D 3/162; C11D 3/373; C11D 3/3757; C11D 3/48; C09D 5/00; C09D 5/14; C09D 7/61
See application file for complete search history.

(56) References Cited

U.S. PATENT DOCUMENTS

| | | | |
|---|---|---|---|
| 7,067,104 B2 | 6/2006 | Sandhage | |
| 9,083,010 B2 | 7/2015 | Lockett et al. | |
| 12,091,577 B2 * | 9/2024 | Schierlmann | A01N 59/16 |
| 2005/0126428 A1 | 6/2005 | Lee | |
| 2015/0328490 A1 | 11/2015 | McDaniel | |
| 2017/0164610 A1 | 6/2017 | Mathis | |
| 2017/0247551 A1 * | 8/2017 | Li | C04B 22/06 |

FOREIGN PATENT DOCUMENTS

| | | | | |
|---|---|---|---|---|
| CN | 111004539 A | 4/2020 | | |
| WO | 2020112117 A1 | 6/2020 | | |
| WO | WO 2020/112117 | * | 6/2020 | A61L 9/20 |

OTHER PUBLICATIONS

International Search Report and Written Opinion re: PCT/US2021/035718 issued Oct. 26, 2021.
Extended European Search Report; Office Action, Apr. 26, 2024, 19 pages.
Ouwehand Judith et al, "Titania-functionalized diatom frustules as photocatalyst for indoor air purification", vol. 226, Dec. 26, 2017, pp. 303-310, XP085636136, ISSN: 0926-3373, DOI 10.1016//J.APCATB.2017 12 063.
Erik Van Eynde et al, "Biotemplated diatom silica-titania materials for air purification", Photochemical & Photobiological Sciences, vol. 12, No. 4, Jan. 1, 2013, 5 pages.

* cited by examiner

*Primary Examiner* — Brian P Mruk
(74) *Attorney, Agent, or Firm* — Amy E. Allen Hinson; Parker Poe Adams & Bernstein LLP

(57) ABSTRACT

An air purifying coating system and method for making same having a carrier agent and a diatomic frustule particle dispersion combined with the carrier agent. The diatomic frustule particle dispersion may include diatomic frustule zinc oxide particles, diatomic frustule titanium dioxide particles, or combinations thereof. The coating system may include 70-99.9 weight percent carrier agent and 0.1-30 weight percent diatomic frustule particle dispersion. The carrier agent of the coating system may include a cleaning agent or a polishing agent. The diatomic frustule particle dispersion may include 1-35 micron particle size diatomic frustule particles combined with water and dispersion additive. The dispersion may further include an anti-settling additive, a rheology additive, and/or or a defoamer.

34 Claims, No Drawings

AIR PURIFYING COATING SYSTEM AND METHOD FOR MAKING SAME

BACKGROUND

The present invention relates generally to the field of coatings. More particularly, the present invention relates to an air purifying coating system having a diatomic frustule particle dispersion combined with a carrier agent, such as a cleaning and/or a polishing agent. The diatomic frustule particle dispersion may be zinc oxide, titanium oxide, or combinations thereof. The present invention also relates to a method of making the air purifying coating system. The air purifying coating system may be applied to substrates, such as wood, laminate, or synthetic surfaces such as PVC, vinyl, linoleum, or hard surfaces such as concrete, stone, terrazzo, granite, or marble and reduces toxins, such as volatile organic compounds (VOCs), from the surrounding air environment.

Indoor air quality continues to be an important area of concern. Indoor air pollutants can come from sources such as carpets, furnaces, furniture, insulation, pets, refuse, and fuels from the garage. While current technology in home building makes houses more air tight, this can trap VOCs within a house and lead to situations such as sick house syndrome.

Products are available that claim to clean VOCs from the indoor air. Many of these available products however have shortcomings. For example, many of these products become inactive as they fill with impurities and lose their VOC reduction efficacy.

Thus there is a need for easy to use products that provide lasting reductions of VOCs and toxins from indoor air environments.

SUMMARY

The following presents a simplified summary of the invention in order to provide a basic understanding of some aspects of the invention. This summary is not an extensive overview of the invention. It is not intended to identify key or critical elements of the invention or to delineate the scope of the invention; its sole purpose is to present concepts of the invention in a simplified form as a prelude to the more detailed description that is subsequently presented.

The present invention includes an air purifying coating system. In one embodiment of the invention, the air purifying coating system includes a carrier agent and a diatomic frustule particle dispersion combined with the carrier agent, wherein the dispersion may be a diatomic frustule zinc oxide particle dispersion, a diatomic frustule titanium oxide particle dispersion, or a combination thereof. In one embodiment of the present invention, the coating system includes 70-99.9 weight percent carrier agent and 0.1-15 weight percent diatomic frustule particle dispersion.

In an embodiment of the air purifying coating system of the present invention, the diatomic frustule particle dispersion may include diatomic frustule particles having a particle size of 1-35 microns. In a further embodiment of the present invention, the diatomic frustule particle dispersion may include water, diatomic frustule particles, and a dispersion additive. The diatomic frustule particle dispersion may also include an anti-settling additive, a rheology additive, and/or a defoamer.

In one embodiment of the present invention, the diatomic frustule particle dispersion includes 50-75 weight percent water, 20-50 weight percent diatomic frustule particles, 1-10 weight percent dispersion additive, such as a copolymer of pigment affinic groups, and 0.1-2 weight percent rheology additive, such as modified urea resin.

In an embodiment of the air purifying coating system of the present invention, the carrier agent may be a cleaning agent. Further, the coating system of the present invention may include 95-99.9 weight percent cleaning agent and 0.1-5.0 weight percent diatomic frustule particle dispersion. In an embodiment of the air purifying coating system of the present invention, the cleaning agent may include acrylic resin, surfactant, and hydrotropes. In another embodiment of the air purifying coating system of the present invention, the cleaning agent may include 80-97 weight percent water, 0.5-5 weight percent acrylic resin, such as alkali-soluble metal-complexed acrylic copolymer, 0.1-1 weight percent hydrotrope, 0.1-3 weight percent emulsifier, such as alkyl polyethylene glycol ether made from a C10-Guerbet Alcohol and ethylene oxide, 0.1-1 weight percent freeze thaw agent, such as a surfactant blend, 0.1-1 weight percent flow additive, such as polyether-modified, hydroxy-functional polydimethylsiloxane, and/or polyether modified siloxane, 0.1-1 weight percent defoamer, such as foam destroying polysiloxanes, 0.1-1 weight percent polyether modified siloxane surface modifier, 0.1-1 weight percent anti-settle additive, such as a modified urea resin, and 0.1-0.5 weight percent biocide, such as a blend of benzoisothiazilinone and methylisothiazilinone. The dispersion may be a diatomic frustule zinc oxide particle dispersion, a diatomic frustule titanium oxide particle dispersion, or a combination thereof.

In an embodiment of the air purifying coating system of the present invention, the carrier agent may be a polishing agent. Further, the coating system of the present invention may include 70-99.9 weight percent polishing agent and 0.1-30 weight percent diatomic frustule particle dispersion. In an embodiment of the air purifying coating system of the present invention, the polishing agent may include water, binder, freeze thaw agent, solvent, defoamer, and a surface modifier. In one embodiment, the binder may be acrylic copolymer resin. Alternatively, the binder may also be polyurethane resin. In another embodiment of the air purifying coating system of the present invention, the polishing agent may include 45-95 weight percent water, 3-53 weight percent acrylic copolymer and acrylic copolymer, 1-5 weight percent solvent, 0.0-1 weight percent freeze thaw additive, 0.1-1 weight percent anti-settling additive, such as a modified urea resin, 0.01-1 weight percent flow additive, such as polyether modified siloxane and/or a fluorinated surfactant, 0.01-1 weight percent defoamer, 0.01-0.5 weight percent biocide, 0.1-3 weight percent wax additive, and 0.01-0.1 weight percent dispersant, such as a copolymer of pigment affinic groups. The dispersion may be a diatomic frustule zinc oxide particle dispersion, a diatomic frustule titanium oxide particle dispersion, or a combination thereof.

The present invention also includes a method of manufacturing an air purifying coating system. In one embodiment of the invention, the method includes the steps of providing diatomic frustule particles, wherein the particles are diatomic frustule zinc oxide particles, diatomic frustule titanium oxide particles, or a combination thereof, combining the diatomic frustule particles with water and a dispersing additive to form a diatomic frustule particle dispersion, providing a carrier agent, and combining the carrier agent and the diatomic frustule particle dispersion to form the air purifying coating system of the present invention.

In an embodiment of the method of the present invention, the diatomic frustule particles have a particle size of 1-35 microns. Further, the method of the present invention may further include the step of milling the diatomic frustule particles to a particle size of 1-35 microns. In an embodiment of the present invention, the method may further include combining the diatomic frustule particles with a rheology additive and a defoamer to form the dispersion. In an embodiment of the method of the present invention, the method may include combining 50-75 weight percent water, 20-50 weight percent diatomic frustule particles, and 1-10 weight percent dispersing additive to form the diatomic frustule particle dispersion.

The method of the present invention may include combining 85-99.9 weight percent carrier agent and 0.1-15 weight percent diatomic frustule particle dispersion. In one embodiment of the method of the present invention, the carrier agent may be a cleaning agent. Further, the method may include combining 95-99.9 weight percent cleaning agent with 0.1-5 weight percent diatomic frustule particle dispersion. In another embodiment of the method of the present invention, the carrier agent may be a polishing agent. Further, the method may include combining 70-99.9 weight percent polishing agent with 0.1-10 weight percent diatomic frustule particle dispersion. In connection with the cleaning agent or the polishing agent, diatomic frustule particles may be diatomic frustule zinc oxide particles, diatomic frustule titanium oxide particles, combinations thereof.

Further features of the present invention will be apparent from the description that follows. After review, such features may in part be obvious from the description or may be learned by practice of the invention. It is to be understood that both the foregoing general description and the following detailed description are exemplary and explanatory only and are not restrictive of the invention, as claimed.

DETAILED DESCRIPTION OF REPRESENTATIVE EMBODIMENTS

The present invention relates to an air purifying coating system and method of making same. The air purifying coating system may be an air purifying cleaner polishing system. For example, the air purifying cleaner polishing system may be in the form of a cleaner and/or polish that is applied to substrates and surfaces. When applied to a substrate or surface, the air purifying coating system preferably reduces indoor air toxins, such as volatile organic compounds. Additionally, the coating system may also provide acceptable chemical resistance, gloss level, scruff resistance, and/or clarity to the surface where it is applied. The air purifying coating system of the present invention may include a carrier agent such as a cleaning agent, a polishing agent, or a cleaning/polishing agent. The air purifying coating system may further include a diatomic frustule particle dispersion combined with the carrier agent, wherein the dispersion may be a diatomic frustule zinc oxide particle dispersion, a diatomic frustule titanium oxide particle dispersion, or a combination thereof. The air purifying coating system of the present invention may be combined with further components and/or additives depending on the intended use of the coating system.

Although primarily described herein in terms of its use as a surface cleaner and/or polish, it will be clear that the air purifying coating system of the present invention may have various other uses. Further, while the air purifying coating system of the present invention is primarily identified as providing beneficial air purifying characteristics when applied to surfaces and substrates, it may also exhibit additional beneficial characteristics and properties.

Unless otherwise stated, the following terms used in the specification and claims have the meanings given below.

As used herein unless otherwise stated, the term "nanoparticle" is given its ordinary and customary meaning in the art and refers to a particle consisting in size between 1-100 nanometers, or $1 \times 10^{-9}$ meters.

As used herein unless otherwise stated, the term "micron" is given its ordinary and customary meaning in the art and refers to a particle having a size between 1-100 microns, or $1 \times 10^{-6}$ meters.

As used herein unless otherwise stated, the term "mill" is given its ordinary and customary meaning in the art and refers to a machine used to reduce pigment particle size to a repeatable and consistent distribution.

As used herein unless otherwise stated, the term "surfactant" refers to an organic polymer with positive or negative charges used to stabilize and separate pigment particles in a solution of water or organic solvent.

As used herein unless otherwise stated, the term "dispersion solution" refers to a solution containing pigment, solvent, defoamers, surfactants, and anti-settling additives.

As used herein unless otherwise stated, the term "polymer/resin" refers to an organic compound used in paints, coatings, and polishes to bind pigments and protect surfaces such as wood, concrete, synthetic surfaces, and natural stone.

As used herein unless otherwise stated, the term "polishing agent" refers to a coating that is used to add protection to a surface such as wood, vinyl, laminate, pvc, linoleum, stone, granite, terrazzo, marble, or concrete floor.

As used herein unless otherwise stated, the term "cleaning agent" refers to a material comprised of surfactants, solvents, water, and polymeric resins.

As used herein unless otherwise stated, the term "particle size analyzer" refers to a device that determines the particles size and count in a solution. The values can be calculated in nanometers or micrometers. The unit being utilized for testing herein is a Accusizer N3000 but other units may be used without departing from the scope of the invention.

As used herein unless otherwise stated, the term "weatherometer" refers to a device used to simulate sunlight exposure in a controlled and accelerated method. The chamber can be controlled to be various temperatures as well as humidity conditions. The unit being utilized for testing herein is a XE1 with an air-conditioned chamber to maintain STP (standard temperature and pressure) conditions but other units may be used without departing from the scope of the invention.

Reference now will be made in detail to embodiments and examples of the present invention. The particular components and amounts thereof recited in these examples, as well as other conditions and details, should not be construed to unduly limit this invention. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. In the examples and discussion throughout this description, all percentages, proportions and ratios are by weight (mass) unless otherwise indicated.

An air purifying coating system and method of making same is disclosed. As stated above, the system may include a carrier agent such as a cleaning agent, a polishing agent, or a cleaning/polishing agent, which is combined with a diatomic frustule particle dispersion. The diatomic frustule particle dispersion may be a diatomic frustule zinc oxide particle dispersion, a diatomic frustule titanium oxide particle dispersion, or a combination thereof. In one embodiment of the air purifying coating system of the present invention, the coating system may comprise 70-99.9 weight percent carrier agent and 0.1-15.0 weight percent diatomic frustule particle dispersion.

The diatomic frustule particle dispersion includes diatomic frustule particles ("DF particles") combined with a dispersion solution. The diatomic frustule particles may be diatomic frustule zinc oxide particles ("DFZnO particles"), diatomic frustule titanium oxide particles ("DFTiO$_2$ particles"), or a combination thereof. The DF particles used in connection with the present invention are preferably nanoparticles. The diatomic frustule particle dispersion ("DF dispersion") is preferably a stable aqueous dispersion for incorporation into a carrier agent, such as cleaners, polishes, and cleaner/polishes.

Prior to forming the DF dispersion, the DF particles may be milled to make the pigment more stable and uniform in solution. The milling may be achieved using an HCP immersion mill from Hockmeyer Corporation, and the media may be zirconium oxide 0.4 mm in size.

A DF dispersion, may include several components to insure the pigment particles are evenly separated and stabilized in solution. Further, the DF dispersion may also utilize components for settling and defoaming. In one embodiment of the DF dispersion of the present invention, the dispersion may include approximately 50-75 weight percent water. The DF dispersion may also include approximately 20-50 weight percent DF particles, such as Diatomix 10-micron powder or diatomic frustule zinc oxide particle powder (ZnO DPA). Further, the DF dispersion may include approximately 1-10 weight percent dispersing additive. The DF dispersion may also include approximately 0.1-2 weight percent rheology additive, such as a nonionic urethane copolymer. Additionally, the DF dispersion may include approximately 0.01-0.2 weight percent of a defoamer to minimize foam generation during the mixing process.

The DF dispersion may be made by combing water with dispersing additive in a container such as a dissolver. Preferably the dispersing additive is added to the water under moderate agitation and mixed for approximately 5 minutes. The rheology additive may then be added under moderate agitation for approximately 10 minutes until the rheology additive is mixed thoroughly. Depending on the foam generation of the dispersion, a defoamer may then be added to keep foam from generating in the mixing process. Finally, the DF particles, such as Diatomix 10-micron powder or diatomic frustule zinc oxide particle powder (ZnO DPA), is preferably sifted into the batch under agitation. The dispersion may then be transferred from the dissolver to an immersion mill, such as a HCP immersion mill. The DF dispersion may then be milled until the effective Hegman particle size is preferably greater than 1 and less than 100 microns or more preferably greater than 6 or less than 20 microns. In one embodiment, the milling speed is approximately 2500-3500 rpms.

Carrier agents of the present invention, including most cleaners, polishes, and cleaner/polishes, typically have a lower viscosity and are lower non-volatile material products than the DF particles. Thus, the DF particles are preferably placed into a dispersion form to aid in incorporating the particles into such lower viscosity and lower non-volatile material agents.

As stated above, carrier agents of the present invention include cleaning agents. When cleaning agents are incorporated into the present invention, an air purifying cleaning system is formed. The cleaning agents of the present invention include both cleaners and refresher products and are typically water-based. Cleaning agents of the present invention preferably include acrylic resins and more preferably include alkali-soluble metal-complexed acrylic copolymer, which have acid values greater than 25 mg KOH. Cleaning agents of the present invention also preferably include surfactants, such as alkyl polyethylene glycol ether made from a C10-Guerbet Alcohol and ethylene oxide. Surfactants are often used for cleaning, degreasing and emulsifying soils and other types of contaminates. In water-based cleaning systems, freeze thaw stability is important to the maintenance of the systems performance. Thus, when water-based cleaning agents are incorporated in connection with the present invention, surfactants that provide freeze thaw stability but do not interfere with system performance may be incorporated. Cleaning agents of the present invention may further utilize hydrotropes for solubilizing hydrophobic compounds.

To insure adequate surface wetting and surface protection of the air purifying cleaning system, surface wetting materials that lower the surface tension of the cleaning agent and provide a uniform layer over the flooring material may be used. Functionalized surface wetting materials may also be used, which can add a level of surface marring protection.

With the use of surfactants, defoaming agents that limit excessive foaminess or bubbling are often incorporated into the air purifying cleaning system of the present invention. Preferably such defoaming agents, such as foam destroying polysiloxanes, have long term efficacy without having an adverse interaction with the surfactants. When incorporating the DF particles into a lower viscosity cleaning agent, a rheology modifier may be used to prevent the DF particles from becoming hardened on the bottom of the container.

Glycol ether solvents, such as dipropylene glycol monomethyl ether, propylene glycol butyl ether, tripropylene glycol methyl ether, and/or diethylene glycol ethyl ether, may be incorporated into the air purifying cleaning system to aid in solubilizing the greases and/or resins in the system.

In one embodiment of the present invention, the cleaning agent of the air purifying cleaning system includes approximately 80-97 weight percent water. Further, the cleaning agent may include approximately 0.5-5 weight percent alkali-soluble metal-complexed acrylic copolymer for adhesion and resolubility. Additionally, the cleaning agent of the present invention may include approximately 0.1-1 weight percent hydrotrope, such as sodium cumene sulfonate. The cleaning agent of the present invention may include surfactants to address cleaning and emulsifying of dirt. In one embodiment, the cleaning agent of the present invention may include approximately 0.1-3 weight percent emulsifiers. For example, approximately 0.1-1 weight percent alkyl polyethylene glycol ether made from a C10-Guerbet Alcohol and ethylene oxide may be incorporated into the cleaning agent. Specialty additives may also be incorporated into the cleaning agent of the air purifying cleaning system. For example, freeze thaw additives such as approximately 0.1-1 weight percent freeze thaw agents, such as a surfactant blend, flow additives at approximately 0.01-1 weight percent, such as foam destroying polysiloxanes, at approximately 0.1-1 weight percent, surface modifiers at approximately 0.1-1 weight percent, anti-settle additives at approximately 0.1-1 weight percent, approximately 0.1-0.5 weight percent biocides, such as a blend of benzoisothiazilinone and methylisothiazilinone, and solvents for resin solubility may be incorporated. In an embodiment of the present invention, approximately 0.1-5 weight percent DF dispersion may be incorporated into the cleaning agent to form the air purifying cleaning system of the present invention.

Polishing agents may also be used as carrier agents of the present invention. When polishing agents are incorporated into the present invention, an air purifying polishing system is formed. Polishing agents may be used to add protection to a surface such as a wood, synthetics, stone, and/or other hard surface. For example, polishing agents are used to protect substrates and surfaces from scratches, scuffing, chemical damage and premature failure. Polishing agents may also provide secondary attributes such as glossiness, coloration, and depth of image or clarity. Polishing agents include both polishes and finishes.

Polishing agents of the present invention may be water-based and may include binders, such as polyurethane and/or acrylic resins. Such products preferably provide durability against scuffing, chemical resistance, and/or adhesion to various substrates.

In water-based polishing systems, freeze thaw stability is important to the maintenance of the systems performance. Thus, when water-based polishing agents are incorporated in the system of the present invention, surfactants that provide freeze thaw stability but do not interfere with system performance may be incorporated. Examples of such products include tributoxyethylphosphate, butyl hydroxybutanoate, and propylene glycol.

To insure adequate surface wetting and surface protection of the air purifying polishing system, surface wetting materials that lower the surface tension of the polishing agent and provide a uniform layer over the flooring material may be used. Functionalized surface wetting materials may also be used, which can add a level of surface marring protection.

Similar to the cleaning systems of the present invention, foam destroying polysiloxanes that limit excessive foaminess or bubbling often caused by surfactants may be incorporated into the air purifying polishing system of the present invention. Preferably such defoaming agents have long term efficacy without having an adverse interaction with the surfactants. Furthermore, when incorporating the DF particles into a lower viscosity polishing agent, a rheology modifier may be used to prevent the DF particles from becoming hardened on the bottom of the container.

Solvents may be incorporated into the air purifying polishing system to aid in solubilizing the resins in the system. Examples of solvents used in connection with the present invention include glycol ethers, such as dipropylene glycol monomethyl ether, propylene glycol butyl ether, tripropylene glycol methyl ether, and/or diethylene glycol ethyl ether.

In one embodiment of the present invention, the polishing agent of the air purifying polishing system includes approximately 40-95 weight percent water. Further, the polishing agent may include approximately 3-53 weight percent binders, or more preferably 20-50 weight percent binders, such as acrylic and urethane components. The polishing agent of the present invention may include approximately 1-9 weight percent solvent composition, or more preferably 1-5 weight percent solvent. Moreover, the polishing agent may further include approximately 0.1-1 weight percent anti-settling agent, such as a modified urea resin, approximately 0.1-1 weight percent flow and leveling agents, such as polyether modified siloxane, 0.01-0.05 weight percent fluorinated surfactant, and/or approximately 0.01-1.0 weight percent foam destroying polysiloxanes. The polishing agent may also include approximately 0.1-1 weight percent freeze thaw agent, such as a surfactant blend or propylene glycol. The polishing agent may include approximately 0.1-1.0 weight percent rheology modifier, such as a nonionic urethane copolymer, for leveling. Approximately 0.01-0.5 weight percent biocide, such as a blend of benzoisothiazilinone and methylisothiazilinone, may be incorporated into the polishing agent of the present invention for the prevention of microbial attack. Further, approximately 0.1-5 weight percent of a wax additive, such as polyethylene blend, may be added to the polishing agent of the present invention to provide marring resistance. The polishing agent may also include 0.01-0.1 weight percent dispersant such as copolymer of pigment affinic groups.

In another embodiment of the present invention, the polishing agent of the air purifying polishing system includes approximately 40-75 weight percent water. Further, the polishing agent may include approximately 23-58 weight percent binders, such as acrylic and urethane components. The polishing agent of the present invention may include approximately 1-5 weight percent solvent composition, such as glycol ethers. Moreover, the polishing agent may further include approximately 0.1-3 weight percent freeze thaw agent, such as a modified phospate, approximately 0.1-1 weight percent anti-settling agent, such as a modified urea resin, approximately 0.1-1 weight percent flow and leveling agents, such as polyether modified siloxane, 0.01-0.05 weight percent fluorinated surfactant, and/or approximately 0.01-1.0 weight percent defoamer, such as foam destroying polysiloxanes. The polishing agent may further include approximately 0.1-1.0 weight percent rheology modifier, such as a nonionic urethane copolymer, for leveling. Approximately 0.01-0.5 weight percent biocide, such as a blend of benzoisothiazilinone and methylisothiazilinone, may be incorporated into the polishing agent of the present invention for the prevention of microbial attack. Further, approximately 0.1-4 weight percent of a wax additive, such as polyethylene blend, may be added to the polishing agent of the present invention to provide marring resistance. The polishing agent may also include 0.01-0.2 weight percent dispersant such as copolymer of pigment affinic groups.

In yet a further embodiment of the present invention, the polishing agent of the air purifying polishing system includes approximately 40-75 weight percent water. Further, the polishing agent may include approximately 20-50 weight percent acrylic copolymer and approximately 5-30 weight percent polyurethane dispersion polymer. The polishing agent of the present invention may include approximately 1-5 weight percent solvent composition, such as glycol ethers. Moreover, the polishing agent may further include approximately 1-7 weight percent matting pigment, approximately 1-5 weight percent rheology additive, such as bentonite clay, approximately 0.1-1 weight percent flow and leveling agents, such as polyether modified siloxane, approximately 0.01-0.05 weight percent fluorinated surfactant, and/or approximately 0.01-1.0 weight percent defoamer, such as foam destroying polysiloxanes. The polishing agent may include approximately 0.1-1.0 weight percent rheology modifier, such as a nonionic urethane copolymer, for leveling. Approximately 0.01-0.5 weight percent biocide, such as a blend of benzoisothiazilinone and methylisothiazilinone, may be incorporated into the polishing agent of the present invention for the prevention of microbial attack. Further, approximately 1-15 weight percent of a crosslinker, such as a polyisocyanate polymer, may be included for further curing. The polishing agent may also include approximately 0.01-0.1 weight percent of a dispersant for additional stabilization of the of the DF particles in the DF dispersion. In an embodiment of the present invention, approximately 0.1-10 weight percent DF dispersion may be incorporated with the polishing agent to form the air purifying polishing system of the present invention. The DF dispersion may include, DFZnO particles, DFTiO$_2$ particles, or combinations thereof.

Because the carrier agents of the present invention are typically cleaning agents and/or polishing agents, the coatings of the present invention are often primarily used for cleaning or polishing various substrates and surfaces, such as for wood, concrete, laminate, PVC, vinyl, linoleum, and/or natural stone, in addition to the secondary benefit of providing a VOC reducing coating system.

The coating systems of the present invention preferably reduce volatile organic compound levels in the air. For example, the coating system preferably reduces volatile organic compounds, such as ketones, amines, alcohols, and aldehydes that result in poor indoor air quality. In addition to reducing volatile organic compounds from the indoor air, the coating systems of the present also preferably maintain or improve surface cleaning and/or polishing properties, such as surface sheen, chemical resistance, surface clarity, and cleaner/polish flow and leveling. The reduction of volatile organic compounds in the surrounding air may be activated when the coating system is applied to a surface and encounters either indoor lighting or natural lighting, such as sunlight.

The present invention includes a method of forming an air purifying coating system of the present invention. In one embodiment of the invention, the method includes the steps of providing diatomic frustule particles, such as diatomic frustule zinc oxide particles, diatomic frustule titanium dioxide particles, or combinations thereof, combining the diatomic frustule particles with water and a dispersing additive to form a diatomic frustule particle dispersion, providing a carrier agent, and combining the carrier agent and the diatomic frustule particle dispersion to form the air purifying coating system of the present invention.

In an embodiment of the method present invention, the diatomic frustule particles have a particle size of 1-35 microns. Further, the method of the present invention may further include the step of milling the diatomic frustule particles to a particle size of 1-35 microns. In an embodiment of the present invention, the method may further include combining the diatomic frustule particles with an anti-settling additive, a rheology additive and/or a defoamer to form the dispersion. In an embodiment of the method of the present invention, the method may include combining 50-75 weight percent water, 20-50 weight percent diatomic frustule particles, 0.1-5 weight percent anti settle additive, 0.1-2 weight percent foam destroying polysiloxanes, and 1-10 weight percent dispersing additive to form the diatomic frustule particle dispersion.

The method of the present invention may include combining 85-99.9 weight percent carrier agent and 0.1-15 weight percent diatomic frustule particle dispersion. In one embodiment of the method of the present invention, the carrier agent may be a cleaning agent. Further, the method may include combining 95-99.9 weight percent cleaning agent with 0.1-5 weight percent diatomic frustule particle dispersion. The diatomic frustule particle dispersion may be a diatomic frustule zinc oxide particle dispersion, a diatomic frustule titanium dioxide particle dispersion, or a combination thereof. In another embodiment of the method of the present invention, the carrier agent may be a polishing agent. Further, the method may include combining 90-99.9 weight percent polishing agent with 0.1-10 weight percent diatomic frustule particle dispersion.

Having generally described this instant disclosure, a further understanding can be obtained by reference to certain specific examples illustrated below which are provided for purposes of illustration only and are not intended to be all inclusive or limiting unless otherwise specified.

TESTING & EXAMPLES

The preparation, identification, and testing of example compositions of this disclosure are further described below. The particular materials and amounts thereof recited in these examples, as well as other conditions and details, should not be construed to unduly limit this invention.

Nanoparticle functionalized diatomic frustule material was obtained from Diatomix Incorporated and tested for use in connection with the present invention. The material was a cream-colored powder and had a particle size of approximately 10 microns. When the material was placed into water, the particle size was measured at approximately 15 microns. Measurements were taken using an Accusizer N3000. The particle size distribution was from 1-20 microns on the raw Diatomix DPA52, 10-micron powder. The material did not stay in solution and instead started to immediately settle into a very course grainy appearance in solution. The material was then milled to make the pigment more stable and uniform in solution.

A DFTiO$_2$ particle dispersion was then formed using the Diatomix material after milling. The dispersion was created by combining 50-75 weight percent water with 1-10 weight percent dispersing additive under moderate agitation in a dissolver. The water and dispersing additive were mixed for five minutes. A rheology additive in the amount of 0.1-2 weight percent was then mixed in at moderate agitation for 10 minutes until the rheology additive was thoroughly mixed in the dispersion. A defoamer was then added to keep foam from generating in the mixing process. Approximately 20-50 weight percent of the milled Diatomix material was then sifted into the batch under agitation and then transferred from the dissolver to an HCP immersion mill. The dispersion was milled at a speed of 2500-3500 rpms until the effective Hegman particle size was greater than 6 or less than 20 microns.

Testing was performed on both an air purifying cleaning system and an air purifying polish system to determine the air purifying capabilities of each. Such testing was done by Research Triangle Park Laboratories in Raleigh, North Carolina.

The first test was directed to an air purifying cleaning system of the present invention. A first control sample with cleaning agent and no DFTiO$_2$ particle dispersion was analyzed and a second active sample with cleaning agent and DFTiO$_2$ particle dispersion was analyzed for comparative purposes. The samples were tested for VOC degradation using ASTM D6670 "Standard Practice for Full-Scale Chamber Determination of Volatile Organic Emissions from Indoor Materials/Products" by introducing known concentrations of selected VOCs into 27-liter glass chambers. Two T8 LED light fixtures, which were four feet, were placed outside of the chambers about six inches from the chambers. The lights were placed next to each other and were operated for the entire test period. The samples were applied directly to glass plates (7 inches×14 inches) with three coat layers applied and then cured. The weight of the three coat layers was 0.1 grams determined by weighing the glass plates before and after the applications. The samples were then placed into sealable chambers with the coated side towards the lights for 30 minutes. The chambers were sealed and allowed to equilibrate prior the introducing the VOCs. Temperature and relative humidity was monitored throughout the test and was measured at 25° C. and 35-45% relative humidity. At the beginning of each test and prior to introducing VOCs into the chambers, air samples were collected from the chambers to demonstrate that no VOCs were in the chamber prior to conducting the test. Known amounts of the formaldehyde (2.5 ppm) and methyl mercaptan (1.0 ppm) were then introduced into the chambers. Chamber air samples were then again collected and analyzed at 1 hour, 24-hour, 48-hour, and 72-hour time periods for the specific VOCs introduced. Table 1 below sets forth the results of VOC air sample testing of the control sample and active sample at the various time periods.

TABLE 1

| Time Point | Formaldehyde Control Sample | Formaldehyde Active Sample | Methyl Mercaptan Control Sample | Methyl Mercaptan Active Sample |
| --- | --- | --- | --- | --- |
| 1 hour | 2.50 ppmv | 2.50 ppmv | 1.00 ppmv | 1.00 ppmv |
| 24 hour | 2.24 ppmv | 2.41 ppmv | 0.99 ppmv | 0.64 ppmv |
| 48 hour | 2.13 ppmv | 1.82 ppmv | 0.42 ppmv | 0.34 ppmv |
| 72 hour | 2.36 ppmv | 1.65 ppmv | 0.37 ppmv | 0.24 ppmv |

As set forth above in Table 1, the test chamber having the active sample, which includes the air purifying cleaning system of the present invention, had approximately 15 percent less formaldehyde VOC and approximately 19 percent less methyl mercaptan VOC at 48-hours than the control sample having only cleaning agent. Further, the test chamber having the active sample, which includes the air purifying cleaning system of the present invention, had approximately 30 percent less formaldehyde VOC and approximately 35 percent less methyl mercaptan VOC at 72-hours than the control sample having only cleaning agent.

The second test was directed to an air purifying polishing system of the present invention. A first control sample with polishing agent and no DFTiO$_2$ particle dispersion was analyzed and a second active sample with polishing agent and DFTiO$_2$ particle dispersion was analyzed for comparative purposes. The samples were tested for VOCs degradation using ASTM D6670 "Standard Practice for Full-Scale Chamber Determination of Volatile Organic Emissions from Indoor Materials/Products" by introducing known concentrations of selected VOCs into 27-liter glass chambers. Two T8 LED light fixtures, which were four feet, were placed outside of the chambers about six inches from the chambers. The lights were placed next to each other and were operated for the entire test period. The samples were applied directly to glass plates (7 inches×14 inches) with one coat layer applied and then cured. The weight of the one coat layer was 1.0 gram determined by weighing the glass plates before and after the applications. The samples were then placed into sealable chambers with the coated side towards the lights for 30 minutes. The chambers were sealed and allowed to equilibrate prior the introducing the VOCs. Temperature and relative humidity was monitored throughout the test and was measured at 25° C. and 35-45% relative humidity. At the beginning of each test and prior to introducing VOCs into the chambers, air samples were collected from the chambers to demonstrate that no VOCs were in the chamber prior to conducting the test. Known amounts of the formaldehyde (5.0 ppm) and methyl mercaptan (2.5 ppm) were then introduced into the chambers. Chamber air samples were then again collected and analyzed at 24-hour, 48-hour, and 72-hour time periods for the specific VOCs introduced. Table 2 below sets forth the results of VOC air sample testing of the control sample and active sample at the various time periods.

TABLE 2

| Time Point | Formaldehyde Control Sample | Formaldehyde Active Sample | Methyl Mercaptan Control Sample | Methyl Mercaptan Active Sample |
| --- | --- | --- | --- | --- |
| Initial | 5.00 ppmv | 5.00 ppmv | 2.50 ppmv | 2.50 ppmv |
| 24 hour | 4.46 ppmv | 4.68 ppmv | 2.41 ppmv | 2.24 ppmv |
| 48 hour | 4.17 ppmv | 3.99 ppmv | 2.44 ppmv | 1.89 ppmv |
| 72 hour | 3.77 ppmv | 3.30 ppmv | 2.32 ppmv | 1.45 ppmv |

As set forth above in Table 2, the test chamber having the active sample, which includes one of the air purifying polishing systems of the present invention, had approximately 4.3 percent less formaldehyde VOC and approximately 22.5 percent less methyl mercaptan VOC at 48-hours than the control sample having only polishing agent. Further, the test chamber having the active sample, which includes the air purifying polishing system of the present invention, had approximately 12.5 percent less formaldehyde VOC and approximately 37.5 percent less methyl mercaptan VOC at 72-hours than the control sample having only polishing agent.

In a second polish for another application, testing was similarly conducted as in the previous example. Results are illustrated in Table 3.

TABLE 3

| Time Point | Formaldehyde Control Sample | Formaldehyde Active Sample | Methyl Mercaptan Control Sample | Methyl Mercaptan Active Sample |
|---|---|---|---|---|
| Initial | 50.0 ng | 50.0 ng | 6.0 ppmv | 6.0 ppmv |
| 24 hour | 49.3 ng | 39.9 ng | 6.0 ppmv | 4.8 ppmv |
| 48 hour | 41.2 ng | 17.1 ng | 5.4 ppmv | 2.7 ppmv |
| 72 hour | 26.4 ng | 12.7 ng | 2.2 ppmv | 1.4 ppmv |

The polish example in Table 3 is similar to that of Table 2 but with the additional increase in the non-volatile content, a fluorinated surfactant, and additional wax. From the data, the formaldehyde reduction was 19 percent at 24-hours, and took a steep drop to 58 percent at 48-hours, and 51 percent more than the control system at 72-hours. From the methyl mercaptan data, the result was 20 percent at 24-hours, with a steep drop of 50 percent at 48-hours, and finally 37 percent more reduction than the control at the 72 hour point.

A final illustration is a 2-component acrylic-urethane polish coating system. Once again, this system demonstrates the reduction of the airborne chemicals. This data is shown in Table 4.

TABLE 4

| Time Point | Formaldehyde Control Sample | Formaldehyde Active Sample | Methyl Mercaptan Control Sample | Methyl Mercaptan Active Sample |
|---|---|---|---|---|
| Initial | 24.0 ppmv | 24.0 ppmv | 5.0 ppmv | 5.0 ppmv |
| 24 hour | 21.6 ppmv | 21.6 ppmv | ND ppmv | ND ppmv |
| 48 hour | 16.0 ppmv | 16.0 ppmv | 4.7 ppmv | 3.5 ppmv |
| 72 hour | 15.6 ppmv | 12.3 ppmv | 2.5 ppmv | 1.8 ppmv |

The data is slightly different in this example as the system cures under slightly different kinetics. The formaldehyde reduction stayed about constant for the first 48 hours, likely the result of the isocyanate to hydroxyl reaction interfering with the reduction. As curing slowed, the 72-hour value was 21 percent from the control to the active system containing the DFTiO$_2$ particles. The methyl mercaptan reduction was 25 percent at 48-hours and finally 28 percent greater than the control at 72-hours.

While various embodiments and examples of this invention have been described above, these descriptions are given for purposes of illustration and explanation, and not limitation. Variations, changes, modifications, and departures from the systems and methods disclosed above may be adopted without departure from the spirit and scope of this invention. In fact, after reading the above description, it will be apparent to one skilled in the relevant art(s) how to implement the invention in alternative embodiments. Thus, the present invention should not be limited by any of the above described exemplary embodiments.

Further, the purpose of the Abstract is to enable the various patent offices and the public generally, and especially the scientists, engineers, and practitioners in the art who are not familiar with patent or legal terms or phraseology, to determine quickly from a cursory inspection the nature and essence of the technical disclosure of the application. The Abstract is not intended to be limiting as to the scope of the invention in any way.

What is claimed is:

1. An air purifying coating system comprising:
    a carrier agent, wherein the carrier agent is a cleaning agent or a polishing agent; and
    a diatomic frustule particle dispersion combined with the carrier agent, wherein the diatomic frustule particle dispersion comprises 50-75 weight percent water and 20-50 weight percent diatomic frustule particles, and wherein the diatomic frustule particles are diatomic frustule zinc oxide particles or a combination of diatomic frustule zinc oxide particles and diatomic frustule titanium dioxide particles.

2. The air purifying coating system of claim 1, wherein the diatomic frustule particles are diatomic frustule zinc oxide particles.

3. The air purifying coating system of claim 1, wherein the carrier agent is a cleaning agent.

4. The air purifying coating system of claim 3, wherein the coating system comprises 70-99.9 weight percent cleaning agent and 0.1-30 weight percent diatomic frustule particle dispersion.

5. The air purifying coating system of claim 3, wherein the cleaning agent comprises water, acrylic resin, surfactant, and hydrotropes.

6. The air purifying coating system of claim 3, wherein the cleaning agent comprises:
    80-97 weight percent water;
    0.5-5 weight percent acrylic resin;
    0.1-1 weight percent hydrotrope;
    0.1-3 weight percent emulsifier;
    0.1-1 weight percent freeze thaw agent;
    0.1-1 weight percent flow additive;
    0.1-1 weight percent defoamer;
    0.1-1 weight percent surface modifier;
    0.1-1 weight percent anti-settle additive; and
    0.1-0.5 weight percent biocide.

7. The air purifying coating system of claim 6, wherein the acrylic resin comprises alkali-soluble metal-complexed acrylic copolymer, the hydrotrope comprises sodium cumene sulfonate, the emulsifier comprises alkyl polyethylene glycol ether made from a C10-Guerbet Alcohol and ethylene oxide, the freeze thaw agent comprises a surfactant blend, the flow additive comprises polyether modified siloxane, the defoamer comprises polysiloxanes, the surface modifier comprises polyether modified siloxane, the anti-settle additive comprises a modified urea resin; and/or the biocide comprises a blend of benzoisothiazilinone and methylisothiazilinone.

8. The air purifying coating system of claim 6, wherein the acrylic resin comprises alkali-soluble metal-complexed acrylic copolymer, the hydrotrope comprises sodium cumene sulfonate, the emulsifier comprises ethoxylated fatty alcohols, the freeze thaw agent comprises butyl hydroxybutanoate, the flow additive comprises polyether modified siloxane, the defoamer comprises polysiloxanes, the surface modifier comprises polyether modified siloxane, the anti-settle additive comprises a modified urea resin; and/or the biocide comprises a blend of benzoisothiazilinone and methylisothiazilinone.

9. The air purifying coating system of claim 1, wherein the carrier agent is a polishing agent.

10. The air purifying coating system of claim 9, wherein the coating system comprises 70-99.9 weight percent polishing agent and 0.1-30 weight percent diatomic frustule particle dispersion.

11. The air purifying coating system of claim 9, wherein the polishing agent comprises water, binder, freeze thaw agent, and a surface modifier.

12. The air purifying coating system of claim 11, wherein the binder comprises at least one of acrylic resin and polyurethane resin.

13. The air purifying coating system of claim 9, wherein the polishing agent comprises:
    45-95 weight percent water;
    3-53 weight percent acrylic copolymer and polyurethane resin;
    1-5 weight percent solvent;
    0.1-1 weight percent freeze thaw agent;
    0.1-1 weight percent anti-settling additive;
    0.1-1 weight percent flow additive;
    0.01-1 weight percent defoamer;
    0.1-4 weight percent wax additive;
    0.01-0.5 weight percent biocide; and
    0.01-0.1 weight percent dispersant.

14. The air purifying coating system of claim 13, wherein the solvent comprises glycol ethers, the freeze thaw agent comprises a surfactant blend, the anti-settling additive comprise a modified urea resin, the flow additive comprises polyether modified siloxane, the defoamer comprises polysiloxanes, the wax additive comprises polyethylene blend, the biocide comprises benzoisothiazilinone and methylisothiazilinone, and/or the dispersant comprises a copolymer of pigment affinic groups.

15. The air purifying coating system of claim 13, wherein the solvent comprises glycol ethers, the freeze thaw agent comprises propylene glycol, the anti-settling additive comprise a modified urea resin, the flow additive comprises polyether modified siloxane, the defoamer comprises polysiloxanes, the wax additive comprises polyethylene blend, the biocide comprises benzoisothiazilinone and methylisothiazilinone, and/or the dispersant comprises a copolymer of pigment affinic groups.

16. The air purifying coating system of claim 9, wherein the polishing agent comprises:
    40-75 weight percent water;
    23-58 weight percent acrylic copolymers;
    1-5 weight percent solvent;
    0.1-3 weight percent freeze thaw agent;
    0.1-1 weight percent anti-settling additive;
    0.1-1 weight percent flow additive;
    0.1-4 weight percent wax additive;
    0.01-0.05 weight percent fluorinated surfactant;
    0.01-1 weight percent defoamer;
    0.01-0.5 weight percent biocide; and
    0.01-0.2 weight percent dispersant.

17. The air purifying coating system of claim 16, wherein the solvent comprises glycol ethers, the freeze thaw agent comprises a modified phosphate, the anti-settling additive comprise a modified urea resin, the flow additive comprises polyether modified siloxane, the wax additive comprises polyethylene blend, the defoamer comprises polysiloxanes, the biocide comprises benzoisothiazilinone and methylisothiazilinone, and/or the dispersant comprises a copolymer of pigment affinic groups.

18. The air purifying coating system of claim 9, wherein the polishing agent comprises:
    40-75 weight percent water;
    20-50 weight percent acrylic copolymer;
    5-30 weight percent of polyurethane dispersion polymer;
    1-5 weight percent solvent;
    1-7 weight percent matting pigment;
    1-5 weight percent rheology additive;
    0.1-1 weight percent flow additive;
    0.01-1 weight percent defoamer;
    0.01-0.5 weight percent biocide; and
    1-15 weight percent crosslinker.

19. The air purifying coating system of claim 18, wherein the solvent comprises glycol ethers, the rheology additive comprises bentonite clay, the flow additive comprises polyether modified siloxane, the defoamer comprises polysiloxanes, the biocide comprises benzoisothiazilinone and methylisothiazilinone, and/or the crosslinker comprises a polyisocyanate polymer.

20. The air purifying coating system of claim 1, wherein the diatomic frustule particle dispersion comprises diatomic frustule particles having a particle size of 1-35 microns.

21. The air purifying coating system of claim 1, wherein the diatomic frustule particle dispersion further comprises dispersion additive, rheology additive, and a defoamer.

22. The air purifying coating system of claim 21, wherein the diatomic frustule particle dispersion comprises 1-10 weight percent dispersion additive, and 0.1-2 weight percent rheology additive.

23. The air purifying coating system of claim 1, wherein the diatomic frustule particles are a combination of diatomic frustule zinc oxide particles and diatomic frustule titanium dioxide particles.

24. A method of manufacturing an air purifying coating system comprising the steps of:
    providing diatomic frustule particles, wherein the diatomic frustule particles are diatomic frustule zinc oxide particles or a combination of diatomic frustule zinc oxide particles and diatomic frustule titanium dioxide particles;
    combining 20-50 weight percent the diatomic frustule particles with 50-75 weight percent water and a dispersing additive to form a diatomic frustule particle dispersion;
    providing a carrier agent, wherein the carrier agent is a cleaning agent or a polishing agent; and
    combining the carrier agent and the diatomic frustule particle dispersion to form the air purifying coating system.

25. The method of claim 24 wherein the diatomic frustule particles are diatomic frustule zinc oxide particles.

26. The method of claim 24 wherein the diatomic frustule particles have a particle size of 1-35 microns.

27. The method of claim 24 further comprising the step of milling the diatomic frustule particles to a particle size of 1-35 microns.

28. The method of claim 24, wherein the step of combining carrier agent and the diatomic frustule particle dispersion includes 70-99.9 weight percent carrier agent and 0.1-30 weight percent diatomic frustule particle dispersion.

29. The method of claim 24, wherein the carrier agent is a cleaning agent.

30. The method of claim 29, wherein the step of combining carrier agent and the diatomic frustule particle dispersion includes 95-99.9 weight percent cleaning agent and 0.1-5 weight percent diatomic frustule particle dispersion.

31. The method of claim 24, wherein the carrier agent is a polishing agent.

32. The method of claim 31, wherein the step of combining carrier agent and the diatomic frustule particle dispersion includes 70-99.9 weight percent polishing agent and 0.1-30 weight percent diatomic frustule particle dispersion.

33. The method of claim 24, wherein the step of combining the diatomic frustule particles with water, the combining further includes 0.1-5 weight percent anti-settling additive, 0.1-2 weight percent foam destroying polysiloxane additive, and 1-10 weight percent dispersing additive.

34. The method of claim 24, wherein the diatomic frustule particles are a combination of diatomic frustule zinc oxide particles and diatomic frustule titanium oxide particles.

\* \* \* \* \*